US00PP25043P3

(12) United States Plant Patent
Olesen

(10) Patent No.: US PP25,043 P3
(45) Date of Patent: Nov. 11, 2014

(54) MINIATURE ROSE PLANT NAMED 'POULPAL041'

(50) Latin Name: ***Rosa* hybrid**
Varietal Denomination: Poulpal041

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 181 days.

(21) Appl. No.: 13/507,012

(22) Filed: May 31, 2012

(65) Prior Publication Data

US 2013/0326750 P1 Dec. 5, 2013

(51) Int. Cl.
*A01H 5/00* (2006.01)

(52) U.S. Cl.
USPC ..... Plt./119

(58) Field of Classification Search
CPC ..... A01H 5/0222
USPC ..... Plt./119, 126, 146
See application file for complete search history.

(56) References Cited

PUBLICATIONS

IPM Innovation Title 2009, retrieved on May 27, 2014, retrieved from the Internet at <http://www.messe-essen-presse.de/pressebereich/specialpages/sp.pressetexte.dynamic.download.php.inc.php?lang=en&PID=1715&context=ipm2009> 2 pp.*

* cited by examiner

*Primary Examiner* — June Hwu

(57) ABSTRACT

A new miniature rose plant that has abundant, orange flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpal041'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2006 and the resulting seeds were planted in a controlled environment in Fredensborg, Denmark. The new variety, named 'Poulpal041', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant orange flowers;
2. Vigorous and compact growth;
3. Year-round flowering under glasshouse conditions;
4. Suitability for production from softwood cuttings in pots; and
5. Durable flowers and foliage which make a variety suitable for distribution in the floral industry.

This combination of qualities is not present in previously available commercial cultivars of this type, known to the inventor, and distinguish 'Poulpal041' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpal041' was selected by the inventor as a single plant from the progeny of the hybridization in 2006.

Asexual reproduction of 'Poulpal041' by cuttings was first done by Mogens N. Olesen in the nursery in Fredensborg, Denmark in 2007. This initial and other subsequent propagations conducted in controlled environments have demonstrated that the characteristics of 'Poulpal041' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpal041'. Specifically illustrated in the drawing are flowers at various stages of development, flower in parts, leaves, and stems. Illustrated plants are 3 months in age.

DETAILED DESCRIPTION OF THE VARIETY

The following is a description of 'Poulpal041', as observed in its growth in glasshouses in Burlington, Ontario, Canada. Observed plants are 2 months of age and were cultivated in 15 cm pots. Color references are made using The Royal Horticultural Society (London, England) Colour Chart, 2001, except where common terms of color are used.

For a comparison, several physical characteristics of the rose variety 'Poulymp', U.S. Plant Pat. No. 16,744. are compared to 'Poulpal041' in Chart 1.

CHART 1

| | 'Poulpal041' | 'Poulymp' |
|---|---|---|
| Petalage: | 35 petals | 25 to 30 petals |
| Flower Diameter: | 65 to 70 mm | 60 to 70 mm |
| General Tonality of Flower Color: | Blend of Orange Group 25A and Yellow-Orange Group 15A. | Blend of Yellow-Orange Group 20B, Orange Group 24C, and Yellow-Orange Group 21C |

FLOWER AND FLOWER BUD

Blooming habit: Continuous.

Flower bud:

*Size*.—Upon opening, 30 mm in length from base of receptacle to end of bud. 16 mm in diameter.

*Bud form*.—Ovate.

*Bud color*.—As sepals unfold, petals are Orange-Red Group 31A.

*Sepals*.—Upper Surface: Color: Green Group 138A. Texture: Smooth, moderately pubescent. Lower Surface: Color: Yellow Green Group 144A. Texture: Smooth. Shape: Apex: Cirrhose. Base: Flat at union with receptacle. Margins: Margins have weak foliaceous appendages on three of the five sepals. Size: 35 mm long by 8 mm wide.

*Receptacle*.—Surface Texture: Smooth. Shape: Campanulate. Size: 10 mm tall and 8 mm wide. Color: Yellow Green Group 144A.

*Pedicel*.—Surface: Smooth. Length: 40 to 45 mm. Diameter: Generally 3 mm. Color: Yellow-Green Group 144A. Strength: Moderate.

*Borne*.—Singly.

Flower bloom:

*Fragrance*.—Light floral scent.

*Duration*.—Flowers last up to 28 days.

*Size*.—Flower diameter 65 to 70 mm when open. Flower depth is 25 mm.

*Form*.—General shape is a hybrid tea with a high pointed, tightly closed, center.

*Shape of flower, side view*.—Upon opening, the upper portion is flattened convex. The lower portion concave.

Petalage: Under normal conditions, flowers have 35 petals total, 7 of which are petaloids.

Color:

*General tonality*.—On open flower Orange Group 25A blending with Yellow-Orange Group 15A. No changes.

*Upon opening, petals*.—Inner and outermost petals are Yellow-Orange Group 21A shaded with Orange Group 25A on the upper surface. Upper surface has a petal spot Yellow Group 12A. The lower surface is Orange-Red Group 31A splashed with Yellow-Orange Group 14A. Lower surface has a petal spot Yellow Group 12A.

*After opening, petals*.—Inner and outermost petals remain the same coloration as upon opening.

*Petal reflex*.—Very strong.

*Margin*.—Entire, uniform. No undulations.

*Shape*.—Generally narrow and elliptic. Apex shape: Rounded. Base shape: Acute.

*Size*.—30 mm (l) by 30 mm (w).

*Texture*.—Smooth.

*Thickness*.—Average.

Petaloids:

*Quantity*.—7 on average.

*Shape*.—Irregular, folded, and asymmetric. The apex is rounded with a cleft. The base is acute.

*Color*.—Same as the petals.

*Size*.—20 mm (l) by 10 mm (w).

Reproductive organs:

*Pollen*.—None Observed.

*Anthers*.—Size: 2 mm long. Color: Yellow Group 8A. Quantity: 50 on average.

*Filaments*.—Color: Yellow-Orange Group 14B. Length: About 5 mm.

*Pistils*.—Length: About 6 mm long. Quantity: 40 on average.

*Stigmas*.—Level relative to the length of the filaments and the height of the anthers. Color: Yellow Group 4D.

*Styles*.—Color: Yellow Group 4D.

*Seed formation*.—Not observed.

PLANT

Plant growth: Upright. Plants are about 25 cm in height, and 20 cm wide.

Stems:

*Color*.—Juvenile growth: Yellow-Green Group 144A. Mature growth: Yellow-Green Group 144A.

*Length*.—Canes are 20 cm from the base of the plant to the flowering portion.

*Diameter*.—4 mm.

*Internodes*.—On mature canes, there is an average distance of 30 mm between nodes.

*Surface texture*.—Young and mature wood is smooth.

Prickles: None observed.

Plant foliage:

*Compound leaf size*.—115 mm (l) by 100 mm (w).

*Quantity*.—3 leaves per 10 cm of stem.

*Leaf bearing angle to the stem*.—90 degrees.

*Color of juvenile foliage*.—Upper Leaf Surface: Yellow-Green Group 146B. Lower Leaf Surface: Greyed-Red Group 178A. Anthocyanin: Strong intonations of Greyed-Purple Group 183A occur on upper and lower surfaces of juvenile leaflets.

*Color of mature foliage*.—Upper Leaf Surface: Yellow-Green Group 147A. Lower Leaf Surface: Yellow-Green Group 148B.

Plant leaves and leaflets:

*Stipules*.—Size: About 7 mm in length. Width is normally 2 mm. Shape: Linear, slightly broad based with outward extending apices. Margins: Finely serrated with few stipitate glands. Color: Yellow-Green Group 146B. Surface texture: Smooth on upper and lower surface.

*Petiole*.—Length: 20 mm on average. Diameter: About 2 mm. Upper surface: Yellow-Green Group 146A. Lower surface: Yellow-Green Group 144A. Surface texture: Smooth on upper and lower surface.

*Rachis*.—Length: 30 mm on average. Diameter: About 2 mm. Upper surface: Yellow-Green Group 146A. Lower surface: Yellow-Green Group 144A. Surface texture: Smooth on upper and lower surface.

*Leaflet*.—Number of leaflets: 5 on normal leaves in middle of the stem. Size: 60 mm in length by 40 mm wide. Margin: Serrate. General Shape: Ovate. Apex Shape: Aristate. Base Shape: Round. Texture: Smooth on upper and lower surface. Arrangement: Odd pinnate. Venation: Reticulate. Leaf Gloss: Moderately glossy.

Cold hardiness: The variety is tolerant to USDA Cold Hardiness Zone 6.

Heat tolerance: The variety has been found to be suitable for climate conditions found in the American Horticulture Society heat zone 7.

Disease resistance: Above average resistance to powdery mildew *Sphaerotheca pannosa,* downy mildew *Peronospora sparsa,* rust *Phragmidium* spp., black spot *Diplocarpon rosae,* and *Botrytis cinerea* under normal growing conditions.

The invention claimed is:

1. A new and distinct variety of rose plant of the miniature class named 'Poulpal041', substantially as illustrated and described herein, due to its abundant, orange flowers, vigorous growth, compact habit, suitability for production from softwood cuttings in pots, and durable flowers and foliage that make the variety suitable for distribution in the floral industry.

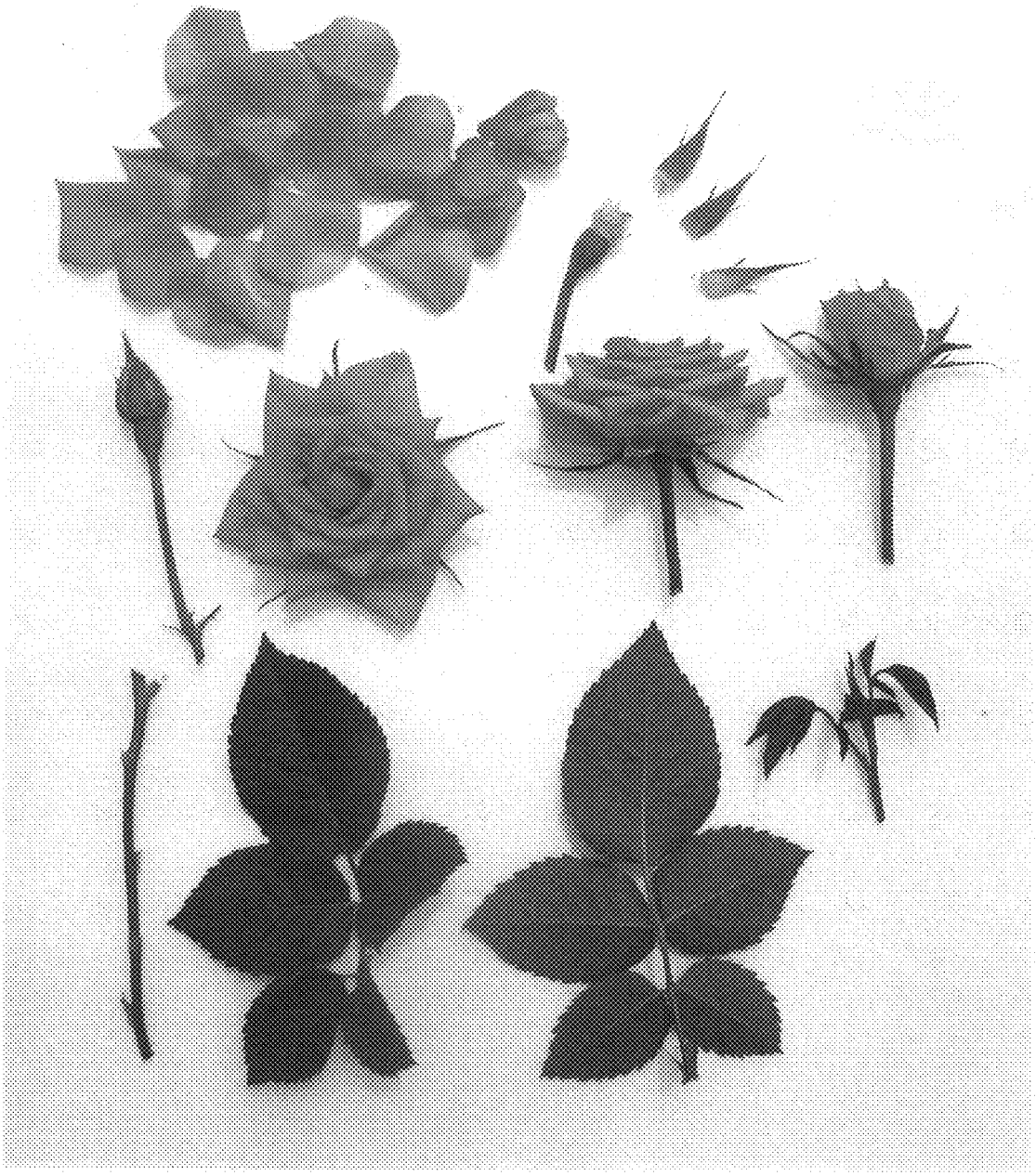

* * * * *